(12) United States Patent
Kawamura et al.

(10) Patent No.: US 10,588,994 B2
(45) Date of Patent: Mar. 17, 2020

(54) LIFE-SCIENCE AND/OR MEDICINAL CHEMISTRY AUTOMATED MANUFACTURING CELL, LIFE-SCIENCE AND/OR MEDICINAL CHEMISTRY AUTOMATED MANUFACTURING METHOD, AND AUTOMATED MANUFACTURING CELL

(71) Applicants: Kabushiki Kaisha Yaskawa Denki, Kitakyushu-shi, Fukuoka (JP); Tanabe Engineering Corporation, Niigata (JP); K.T. MFG. CO., LTD., Tokyo (JP)

(72) Inventors: Yoshinori Kawamura, Kitakyushu (JP); Sakae Yamaguchi, Kitakyushu (JP); Takashi Obunai, Saitama (JP); Takuetsu Oishi, Satte (JP)

(73) Assignees: Kabushiki Kaisha Yaskawa Denki, Fukuoka (JP); Tanabe Engineering Corporation, Niigata (JP)

( * ) Notice: Subject to any disclaimer, the term of this patent is extended or adjusted under 35 U.S.C. 154(b) by 287 days.

(21) Appl. No.: 15/011,666

(22) Filed: Feb. 1, 2016

(65) Prior Publication Data
US 2016/0331857 A1    Nov. 17, 2016

(30) Foreign Application Priority Data
May 11, 2015   (JP) .................. 2015-096842

(51) Int. Cl.
*A61L 2/26*      (2006.01)
*B01L 9/00*      (2006.01)
(Continued)

(52) U.S. Cl.
CPC ........ *A61L 2/26* (2013.01); *A61L 2/07* (2013.01); *A61L 2/10* (2013.01); *A61L 2/16* (2013.01);
(Continued)

(58) Field of Classification Search
CPC ...... A61L 2/07; A61L 2/10; A61L 2/16; A61L 2/24; A61L 2/26; B25J 21/00;
(Continued)

(56) References Cited

U.S. PATENT DOCUMENTS

2002/0064490 A1*  5/2002  Michaelson ............ A61L 2/025
                                                           422/300
2006/0196707 A1*  9/2006  Wang ........................ G01G 3/06
                                                           177/245
(Continued)

FOREIGN PATENT DOCUMENTS

JP    H02-15278 U    1/1990
JP    H03-039081 A   2/1991
(Continued)

OTHER PUBLICATIONS

Office Action dated Feb. 12, 2019, for corresponding JP Patent Application No. 2015-096842.

*Primary Examiner* — Benjamin R Whatley
(74) *Attorney, Agent, or Firm* — HEA Law PLLC

(57) ABSTRACT

Provided is an automated manufacturing cell including: a work booth provided with a work space; a robot arranged in the work booth; a container booth which is connected, in a manner allowing insulation, to each of the work booth and an external space, and is configured to store a work tool and a work subject; and a holder fixation tool which is arranged in the work space, and is configured to detachably fix a holder configured to hold the work tool.

19 Claims, 13 Drawing Sheets

(51) Int. Cl.
*A61L 2/24* (2006.01)
*A61L 2/16* (2006.01)
*A61L 2/07* (2006.01)
*A61L 2/10* (2006.01)
*B25J 9/00* (2006.01)
*B25J 21/00* (2006.01)

(52) U.S. Cl.
CPC ............... *A61L 2/24* (2013.01); *B25J 9/0087* (2013.01); *B25J 21/00* (2013.01)

(58) Field of Classification Search
CPC ... B25J 9/0087; G01N 35/0099; C12M 37/00; B01L 1/04; B01L 46/0091; B01L 2200/082
See application file for complete search history.

(56) References Cited

U.S. PATENT DOCUMENTS

| | | | | |
|---|---|---|---|---|
| 2006/0201810 A1* | 9/2006 | Paschetto | ............... | B01L 3/0244 204/470 |
| 2007/0235644 A1* | 10/2007 | Nakasuji | ............... | G01N 23/225 250/307 |
| 2008/0199353 A1* | 8/2008 | Mlodzinski | ............... | A61J 1/20 422/24 |
| 2013/0184860 A1 | 7/2013 | Ota et al. | | |
| 2013/0331989 A1 | 12/2013 | Umeno et al. | | |
| 2014/0106386 A1 | 4/2014 | Umeno et al. | | |
| 2015/0019003 A1* | 1/2015 | Murakami | ............. | B25J 9/0093 700/217 |
| 2015/0174759 A1 | 6/2015 | Ota et al. | | |
| 2015/0210410 A1 | 7/2015 | Umeno et al. | | |
| 2016/0145671 A1 | 5/2016 | Umeno et al. | | |
| 2017/0137770 A1* | 5/2017 | Sakamoto | ............. | C12M 37/00 |
| 2017/0217027 A1* | 8/2017 | Boucard | ................ | B25J 19/023 |

FOREIGN PATENT DOCUMENTS

| | | | | |
|---|---|---|---|---|
| JP | H03-259075 A | 11/1991 | | |
| JP | H05-123983 A | 5/1993 | | |
| JP | 2000-356642 A | 12/2000 | | |
| JP | 2001-509086 A | 7/2001 | | |
| JP | 2006-341348 A | 12/2006 | | |
| JP | 2008-054690 A | 3/2008 | | |
| JP | 2009-028450 A | 2/2009 | | |
| JP | 2010-105106 A | 5/2010 | | |
| JP | 2010-161931 A | 7/2010 | | |
| JP | 2013-009618 | 1/2013 | | |
| JP | 2013-146853 A | 8/2013 | | |
| JP | 2014-034072 A | 2/2014 | | |
| JP | 2014-178133 A | 9/2014 | | |
| WO | WO-2013157119 A1 * | 10/2013 | ............ | B25J 9/0093 |
| WO | 2014/054183 A1 | 4/2014 | | |
| WO | 2014/132400 A1 | 2/2017 | | |

* cited by examiner

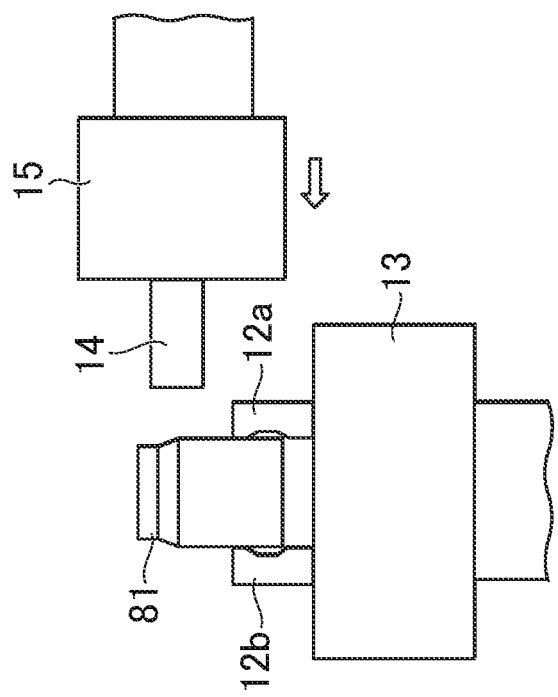
FIG.11C
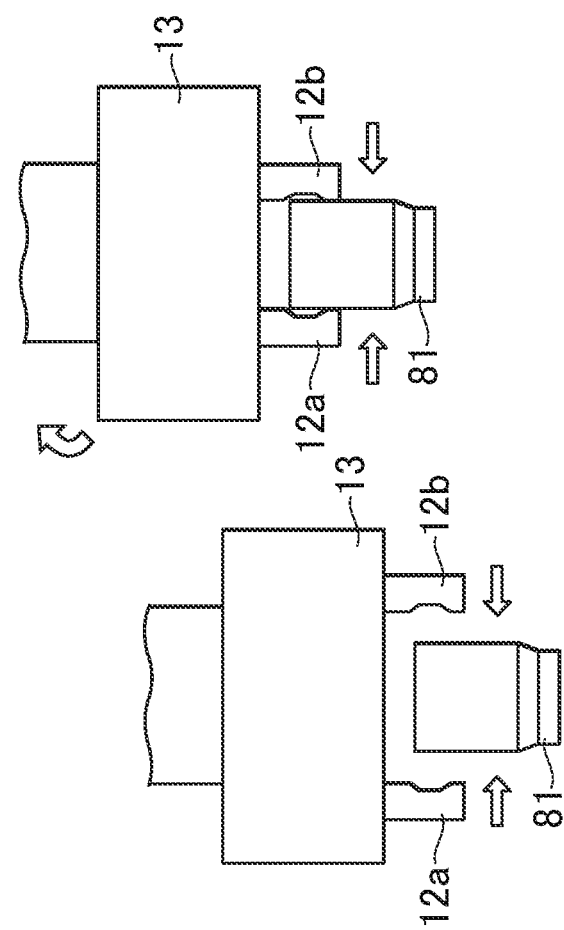
FIG.11B
FIG.11A

LIFE-SCIENCE AND/OR MEDICINAL CHEMISTRY AUTOMATED MANUFACTURING CELL, LIFE-SCIENCE AND/OR MEDICINAL CHEMISTRY AUTOMATED MANUFACTURING METHOD, AND AUTOMATED MANUFACTURING CELL

INCORPORATION BY REFERENCE

The present disclosure contains subject matter related to that disclosed in Japanese Priority Patent Application JP 2015-096842 filed in the Japan Patent Office on May 11, 2015, the entire contents of which are hereby incorporated by reference.

BACKGROUND OF THE INVENTION

Field of the Invention

The present invention relates to a life-science and/or medicinal chemistry automated manufacturing cell, a life-science and/or medicinal chemistry automated manufacturing method, and an automated manufacturing cell.

Description of the Related Art

In International Patent WO2014/054183A1, there is described an automatic preparation system configured to use a robot to use various devices arranged in a safety cabinet, to thereby prepare a medication. In Japanese Patent Application Laid-open No. 2000-356642, there is disclosed a quality control cell configured to use a robot to dispense a radioactive medication contained in a vial, to thereby confirm the quality of the radioactive medication.

SUMMARY OF THE INVENTION

According to one embodiment, there is provided a life-science and/or medicinal chemistry automated manufacturing cell, including: a work booth provided with a work space; a robot arranged in the work booth; a container booth which is connected, in a manner allowing insulation, to each of the work booth and an external space, and is configured to store a work tool and a work subject for life-science and/or medicinal chemistry; and a first holder fixation tool which is arranged in the work space, and is configured to detachably fix a holder configured to hold the work tool.

According to another embodiment, there is provided a life-science and/or medicinal chemistry automated manufacturing method, including: storing, before a start of work, in a container booth connected, in a manner allowing insulation, to each of a work booth in which a work space and a robot are provided, and an external space, a work tool and a work subject for life-science and/or medicinal chemistry; controlling, by a setup controller, the robot to move the work tool and the work subject from the container booth to the work space; controlling, by the setup controller, the robot to fix the holder to a first holder fixation tool which is arranged in the work space, and is configured to detachably fix a holder configured to hold the work tool; and controlling, by a work controller, the robot to use the work tool to work on the work subject.

According to still another embodiment, there is provided an automated manufacturing cell, including: a work booth provided with a work space; a robot arranged in the work booth; a container booth which is connected, in a manner allowing insulation, to each of the work booth and an external space, and is configured to store a work tool and a work subject; and a first holder fixation tool which is arranged in the work space, and is configured to detachably fix a holder configured to hold the work tool.

BRIEF DESCRIPTION OF THE DRAWINGS

FIG. 11A to FIG. 11C are diagrams for illustrating an operation of inverting the vial gripped by one pair of claws, and passing the vial to another pair of claws.

DETAILED DESCRIPTION OF THE EMBODIMENTS

Figure 1:
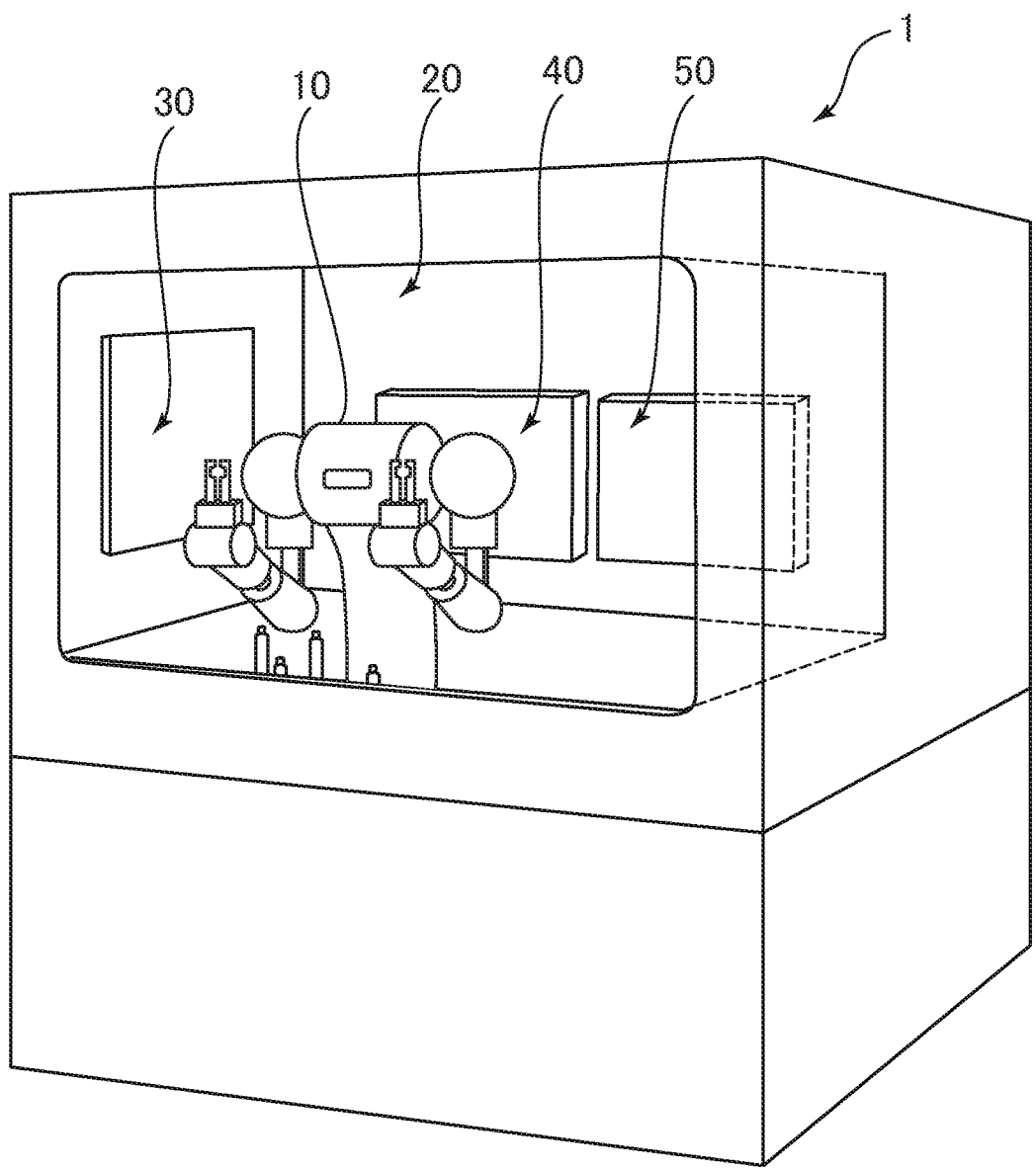
FIG. 1 is an exterior perspective view for illustrating an automated manufacturing cell according to an embodiment.
Figure 2:
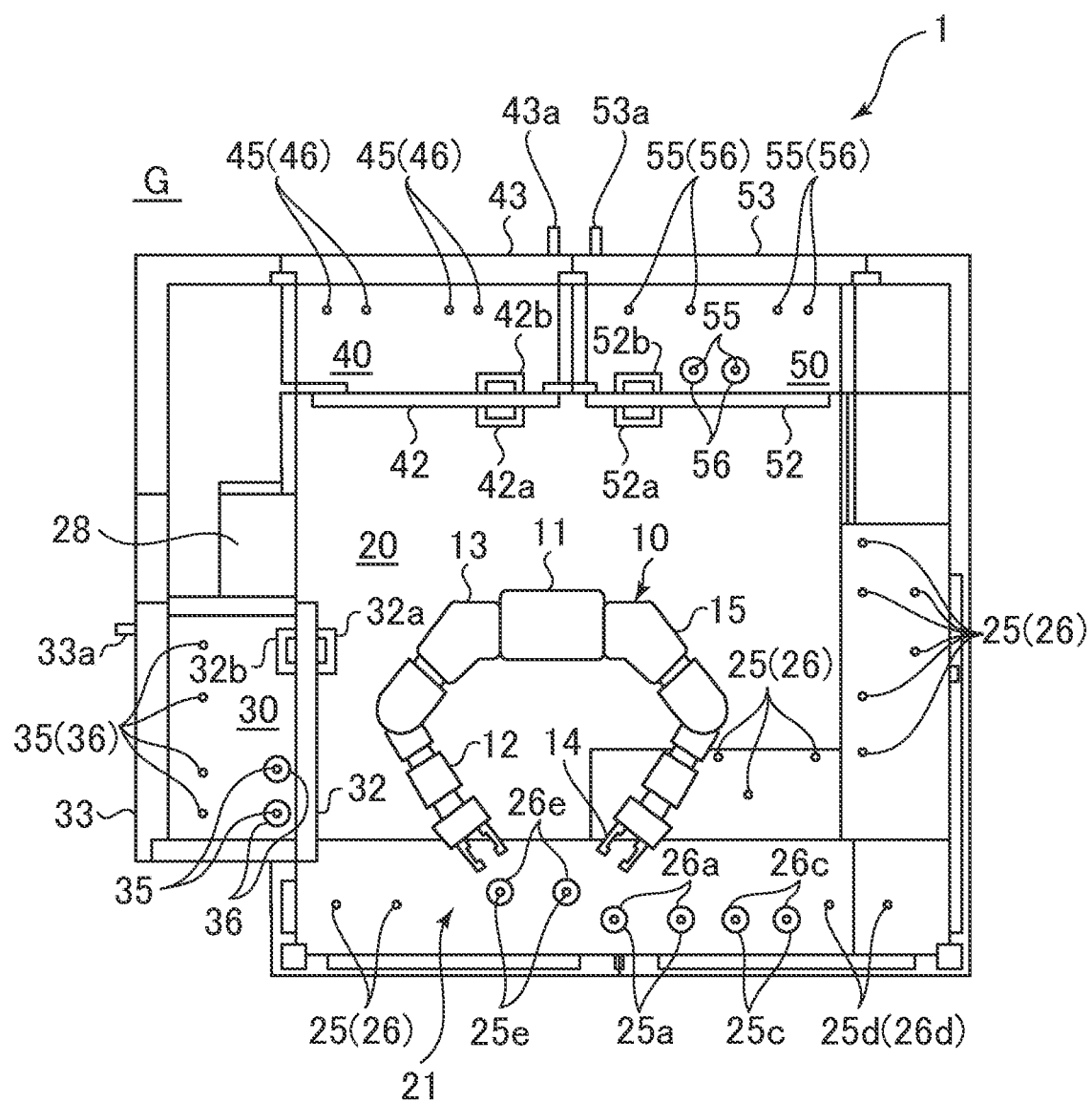
FIG. 2 is a plan view for illustrating the automated manufacturing cell according to the embodiment when viewed from above in a vertical direction.

FIG. 1 is an exterior perspective view for illustrating a life-science and/or medicinal chemistry automated manufacturing cell (hereinafter simply referred to as automated manufacturing cell) according to an embodiment (hereinafter referred to as this embodiment). FIG. 2 is a plan view for illustrating the automated manufacturing cell according to this embodiment when viewed from above in a vertical direction.

The automated manufacturing cell 1 according to this embodiment is used in, for example, fields of life-science and medicinal chemistry requiring application of sterilization treatment to work tools and work subjects in order to avoid contamination during the work, and is configured to control a robot 10 to automatically carry out work on the work subjects by using the work tools in an area kept in an almost aseptic state. Note that, in the following description, the work tool refers to a work tool provided so as to be fixed to a work space 21 during the work, and used as a part of a work device. Moreover, the work subject refers to a subject to which an operation such as processing is applied during the work, and that is a raw material or a part thereof of a product acquired as a result of the work.

The automated manufacturing cell 1 includes the robot 10, a work booth 20, a container booth 30, a container booth 40, and a container booth 50. An inside of the work booth 20 is configured to be kept in an almost aseptic state.

The robot 10 is arranged in the work booth 20. The robot 10 is a so-called articulated robot, and includes a body 11, and a right arm 13 and a left arm 15 provided on the body 11. Moreover, on the right arm 13, a pair of claws 12 (12a and 12b) configured to open and close are provided, and, on the left arm 15, a pair of claws 14 (14a and 14b) configured to open and close are provided.

The robot 10 drives the body 11 and the arms 13 and 15 to make access to the work tools, the work subjects, holders configured to hold the work tools, and the like, and uses the claws 12 or 14 for clamping, hooking, and the like to grip and operate the work tools, the work subjects, and the holders.

In the work booth 20, the work space 21 is provided. A plurality of holder fixation tools 26 each configured to detachably fix the holder configured to hold the work tool are arranged in the work space 21. According to this embodiment, a pin 25 is provided on a distal end of the holder fixation tool 26. Moreover, the plurality of holder fixation tools 26 include holder fixation tools formed on a plane coplanar with a bottom surface of the work space 21 (in this case, the pin 25 is configured to directly protrude from the bottom surface of the work space 21), and are formed so as to be different from one another in height from the bottom surface of the work space 21. The plurality of holder fixation tools 26 are different from one another in height, and when the arms 13 and 15 of the robot 10 make access to one holder, the arms 13 and 15 do not thus interfere with other holders. Therefore, the arms 13 and 15 can be controlled to carry out linear motions, resulting in reduction in an operation period of the robot 10, and easy teaching of the robot 10.

The holder fixation tool 26 fixes the holder or the rack to the work space 21 so as to be detachable and stabilized in a posture by fitting the pins 25 to holes 125 formed on a bottom of the holder configured to hold the work tool, the rack configured to carry the work subject, or the like. Holder fixation tools 36, 46, and 56, which are described later, and on distal ends of which pins 35, 45, and 55 are respectively formed, have the same function. Note that, the number, the arrangement, and the height of the holder fixation tools 26, 36, 46, and 56 are not limited to those described in this embodiment, and may be designed in various ways depending on applications and tools to be used.

Note that, in the following description, the plurality of provided holder fixation tools 26 and pins 25 are distinguished from one another by suffixing reference numerals thereof with lower-case roman characters (such as a and b), but when the holder fixation tools 26 or pins 25 are not shown or a distinguished description is not necessary, the lower-case roman character for suffixing the reference numeral is omitted. The same holds true for the holes 125 and the pins 35, 45, and 55.

The container booth 30 is provided on a right side with respect to the robot 10 facing the work space 21 side, and stores the respective work tools and work subjects. Moreover, in the container booth 30, the plurality of holder fixation tools 36 each including the pin 35 are provided. Moreover, the container booth 30 is connected to the work booth 20 via an open and close door 32 in a manner allowing insulation, and is connected to an external space G via an open and close door 33 in a manner allowing insulation. To the open and close door 32, an outside handle 32a and an inside handle 32b are mounted, and the open and close door 32 is opened/closed by the robot 10 in the automated manufacturing cell 1 hooking the outside handle 32a with the claws 12 or 14 for the operation. Moreover, to the open and close door 33, a handle 33a is mounted, and the open and close door 33 is opened/closed by a person outside the automated manufacturing cell 1. Note that, the open and close door 33 may be automatically opened/closed by another automatic facility or the like.

The container booth 40 is provided on a rear side with respect to the robot 10 facing the work space 21 side, and stores the respective work tools and work subjects. Moreover, in the container booth 40, the plurality of holder fixation tools 46 each including the pin 45 are provided. Moreover, the container booth 40 is connected to the work booth 20 via an open and close door 42 in a manner allowing insulation, and is connected to the external space G via an open and close door 43 in a manner allowing insulation. To the open and close door 42, an outside handle 42a and an inside handle 42b are mounted, and the open and close door 42 is similarly opened/closed by the robot 10 in the automated manufacturing cell 1. Moreover, to the open and close door 43, a handle 43a is mounted, and the open and close door 43 is opened/closed by a person outside the automated manufacturing cell 1.

The container booth 50 is provided on the rear side with respect to the robot 10 facing the work space 21 side, and next to the container booth 40, and stores the respective work tools and work subjects. Moreover, in the container booth 50, the plurality of holder fixation tools 56 each including the pin 55 are provided. Moreover, the container booth 50 is connected to the work booth 20 via an open and close door 52 in a manner allowing insulation, and is connected to the external space G via an open and close door 53 in a manner allowing insulation. To the open and close door 52, an outside handle 52a and an inside handle 52b are mounted, and the open and close door 52 is similarly opened/closed by the robot 10 in the automated manufacturing cell 1. Moreover, to the open and close door 53, a handle 53a is mounted, and the open and close door 53 is opened/closed by a person outside the automated manufacturing cell 1.

According to this embodiment, under a state in which the respective open and close doors are closed to close and seal the container booths 30, 40, and 50, the sterilization treatment is applied to the stored work tools and work subjects. This is because the respective works tools and work subjects brought from the external space G into the container booths 30, 40, and 50 were in contact with hands of persons and the external air, and hence there is a fear for contamination if the work tools and the work subjects are directly used. In each of the container booths 30, 40, and 50, appropriate sterilizers such as a dry heat sterilizer, an autoclave, a chemical clave, and an ultraviolet radiation sterilizer may be installed. In the respective booths 30, 40, and 50, the same sterilizers may be installed, or sterilizers different in type from one another may be installed so that the container booths 30, 40, and 50 may be selectively used depending on contents to be stored. Moreover, for example, when work of handling a substance toxic to the human body such as an anticancer agent is carried out, in order to prevent the toxic substance from leaking to the outside, in each of the container booths 30, 40, and 50, an air conditioning system may be provided so that a differential pressure from the ambience is realized and the inside of the booth is loser in the pressure than the ambience.

Until the completion of the sterilization treatment, a certain period is required after the container booths 30, 40, and 50 were brought into the closed and sealed state. According to this embodiment, there are provided connection detection sensors each configured to detect the connection between one of the container booth 30, 40, and 50 and the external space U and connection inhibitors each configured to inhibit the connection between one of the container booths 30, 40, and 50 and the work booth 20 after the detection of the connection between the one of the container booths 30, 40, and 50 and the external space G by the connection detection sensor, and until the completion of the sterilization treatment in a sterilization area. Therefore, the unintentional opening of the container booth during the sterilization treatment is suppressed, and the sterilization treatment is securely 5 carried out.

As the connection inhibitor, various modes may be employed. For example, such a configuration may be employed that the robot 10 is controlled by a controller 60 (refer to FIG. 3) so that the open and close doors 32, 42, and 52 are not opened until the completion of the sterilization treatment, or such a configuration may be employed that the open and close doors 32, 42, and 52 are physically locked, and the lock cannot be unlocked until the completion of the sterilization treatment.

As illustrated in FIG. 2, in the work booth 20, a temporary placement space 28 is provided at a position close to the container booth 30 and outside the work space 21 and a movable range of the open and close door 32. After the end of the work, when the work tools after the use are returned from the work booth 20 to the container booth 30, by once stocking the plurality of work tools altogether in the temporary placement space 28 and then returning the work tools altogether to the container booth 30, the number of times of loading and storing between the booths can be reduced, thereby reducing an operation period of the robot 10. Note that, the number of the temporary placement spaces 28 is not limited to one, and the temporary placement space 28 may be provided not only at the position close to the container booth 30, but also at positions close to the container booths 40 and 50 and outside movable ranges of the open and close doors 42 and 52.

Figure 3:
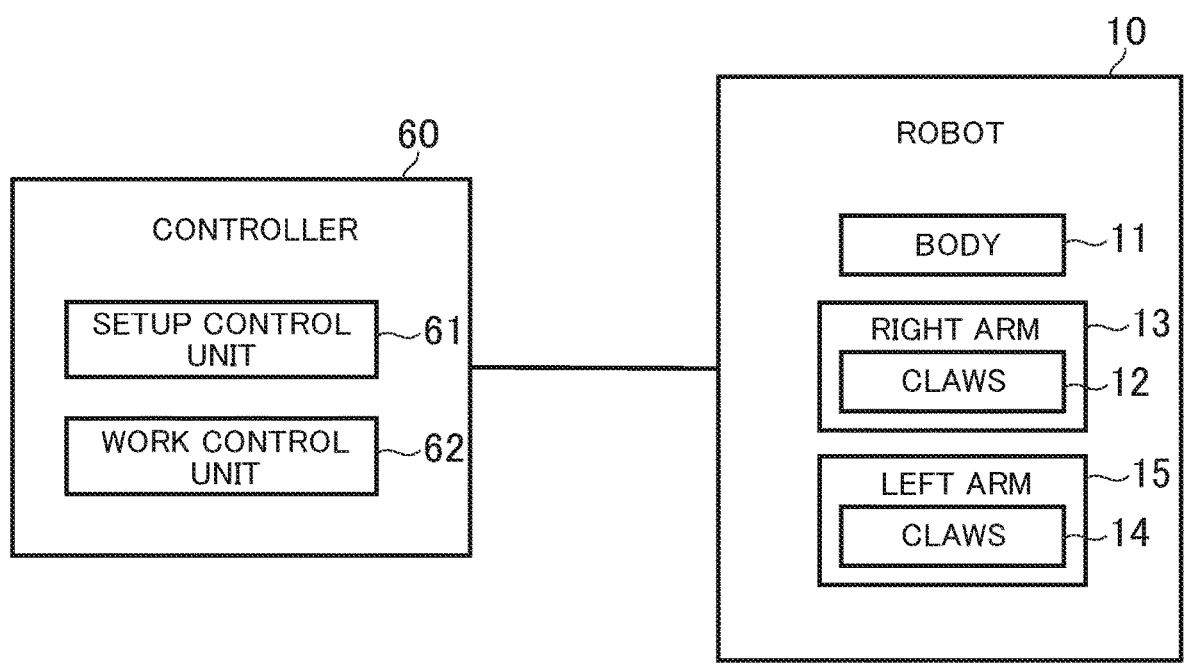
FIG. 3 is a block diagram for illustrating a system configuration of the automated manufacturing cell according to the embodiment.

FIG. 3 is a block diagram for illustrating a system configuration of the automated manufacturing cell according to this embodiment. The automated manufacturing cell 1 includes the robot 10 and the controller 60 configured to control the robot 10. The controller 60 includes a setup controller 61, and a work controller 62. Note that, teaching of an operation program has been carried out for the robot 10 in advance.

The setup controller 61 controls the robot 10 so that the robot 10 moves the holder holding the work tool from the container booth 30, 40, or 50 to the work space 21.

The work controller 62 controls the robot 10 so that the robot 10 uses the work tools to work on the work subjects in the work space 21.

Figure 4:
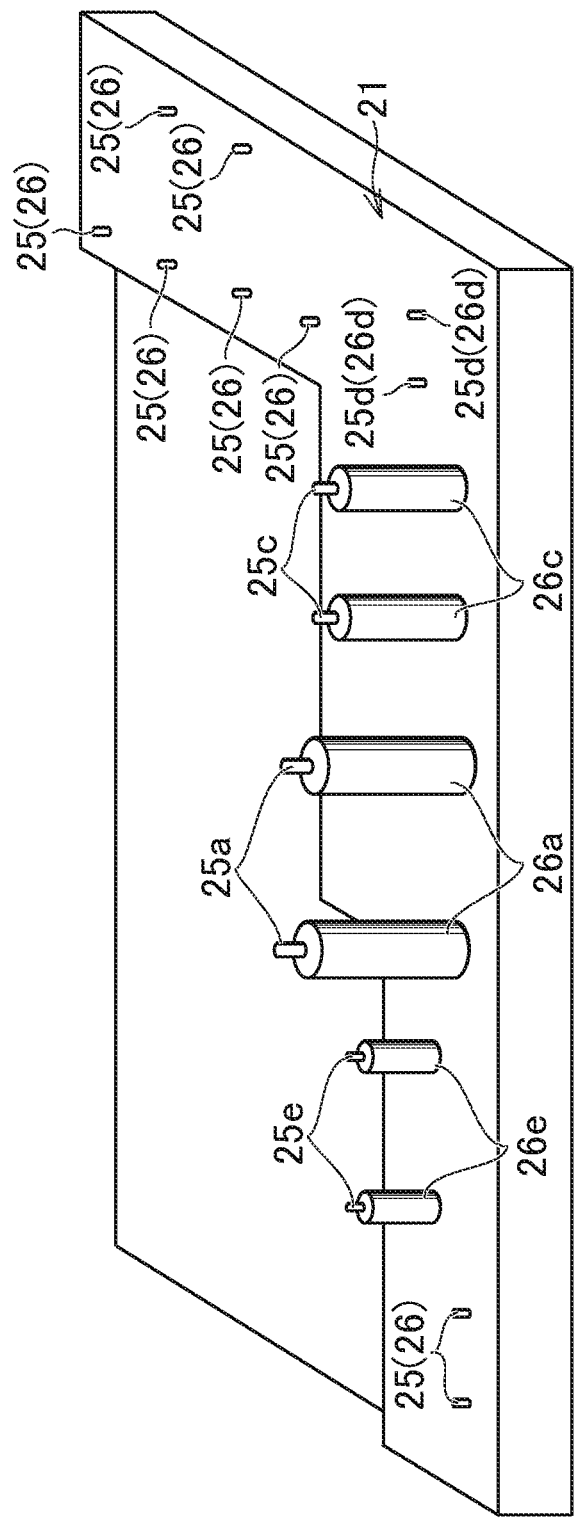
FIG. 4 is a perspective view for illustrating a work space before a start of work and after an end of the work.
Figure 5:
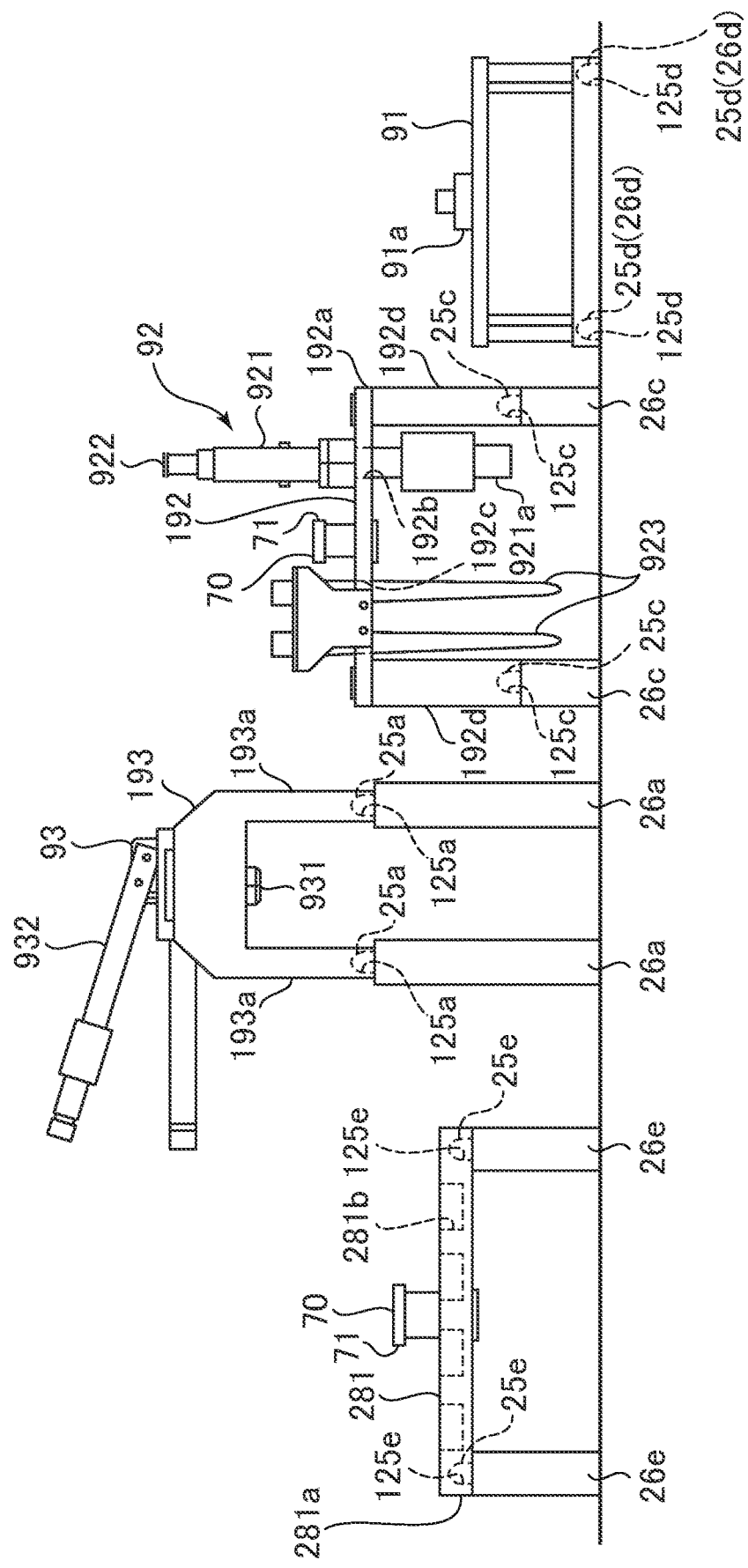
FIG. 5 is a front view for illustrating the work space during the work.

FIG. 4 is a perspective view for illustrating the work space before the start of the work and after the end of the work. FIG. 5 is a front view (a view from a side facing the robot 10 across the work space 21) for illustrating the work space during the work. Note that, in FIG. 4 and FIG. 5, illustration of the robot 10 is omitted.

According to this embodiment, a common gripped portion 70 to be gripped by the claws 12 or 14 is mounted to each holder configured to hold each work tool and each rack configured to carry each work subject. The gripped portion 70 includes a protruded portion 71 on which the claws 12 or 14 are to be hooked.

The gripped portion 70 is common, and thus, a single type of the claws 12 or 14 can be used to grip the various holders and racks. Each holder or rack is moved by driving the body 11 and the arms 13 and 15 of the robot 10 between booths and in the booth while each holder or rack is gripped by the claws 12 or 14.

According to this embodiment, as the work subjects, a drug solution, a vial 81 (refer to FIG. 10), an aluminum cap 82 (refer to FIG. 6), and a rubber plug (not shown) are used. Moreover, as illustrated in FIG. 5, as the work tools, a pipette 92 and a crimp tool 93 are used. Moreover, as holders configured to hold the work tools, a pipet base 192 configured to hold the pipette 92 and a crimp tool base 193 configured to hold the crimp tool 93 are used.

The drug solution is sealed in a drug solution bottle 91 closed by tightening a cap 91a.

The vial 81 is a glass container configured to seal the drug solution. The sealing of the drug solution is carried out by press-fitting the rubber plug to an opening of the vial 81, installing the aluminum cap 82 on the rubber plug, and crimping the aluminum cap 82.

The pipette 92 includes a body 921, a push button 922 provided on a terminal part of the body 921, and a tip 923 detachably provided on a distal end portion 921a of the body 921. The body 921 and the tip 923 of the pipette 92 are each held by the pipette base 192 under a state in which the tip 923 is detached from the body 921 before the use.

The pipette 92 sucks a liquid by placing a distal end of the tip 923 in the liquid under a state in which the tip 923 is mounted on the body 921, once pressing the push button 922 into the body 921, and pulling the push button 922. Further, the liquid is discharged by pushing the push button 922 into the body 921.

Note that, the pipette 92 used in this embodiment has a shape gripped by the claws 12 or 14, but the gripped portion 70 may be mounted to the body 921 depending on a shape of the pipette 92. As a result, the pipette 92 not suitable for the grip by the claws 12 or 14 can be gripped and moved while a stable attitude is maintained. Note that, the pipette 92 is not limited to the tool described in this embodiment as long as a tool can measure, suck, and discharge a liquid, and may be, for example, a tool constructed by integrating the body and the tip to each other. Alternatively, as long as a measurement/discharge tool is configured to have the measurement/discharge function equivalent to that of the pipette 92, the pipette 92 does not always need to be used as the tool, and, for example, a syringe may be used.

The pipette base 192 includes a hold plate 192a configured to hold the body 921 and the tip 922 of the pipette 92, a hold hole 192b which are formed on the hold plate 192a, and into which the body 921 is to be inserted, and hold holes 192c which are formed on the hold plate 192a, and into which the tip 922 is to be inserted. FIG. 5 is an illustration of the hold plate 192a on which the two hold holes 192c capable of holding the tip 923 having the same size are formed, but a pipette base including a hold plate on which a plurality of holes different in size are formed, and which is configured to hold tips different in size depending on a content of the work may be used.

Moreover, the pipette base 192 includes a bifurcated support leg 192d, on bottoms of which holes 125c are respectively formed. The pipette base 192 is detachably fixed to the holder fixation tools 26c by fitting the pins 25c to the holes 125c of the bifurcated support leg 192d. Moreover, the gripped portion 70 is mounted to the hold plate 192a of the pipette base 192.

The crimp tool 93 includes a tightening portion 931 configured to clamp and tighten a crimp subject and a lever 932 configured to operate the tightening portion 931.

The crimp tool base 193 is configured so that the crimp tool 93 is fixed thereto and the crimp tool base 193 and the crimp tool 93 are treated as a unit, and includes a bifurcated support leg 193a, on bottoms of which holes 125a are respectively formed. The crimp tool base 193 is detachably fixed to the holder fixation tools 26a by fitting the pins 25a to the holes 125a of the bifurcated support leg 193a. Moreover, the gripped portion 70 is also mounted to the crimp tool 193 (in FIG. 5, the gripped portion 70 is on a rear side, and is therefore not shown).

Moreover, according to this embodiment, as illustrated in FIG. 5, a vial stand 281 configured to support the vials 81 during work is used. The vial stand 281 of FIG. 5 is under a state in which the vials 81 are not held. The vial stand 281 includes a hold plate 281a configured to hold the vials 81, and hold holes 281b formed in the hold plate 281a and configured to be fit to by the vials 81. Moreover, in the hold plate 281a, holes 125e to which pins 25e are to be fit are formed. Moreover, the gripped portion 70 is mounted to the hold plate 281e of the vial stand 281.

Note that, the support legs of the pipette base 192, the crimp tool base 193, and the vial stand 281 are not limited to the bifurcated legs, and may be configured to have three or more support legs as long as a stable fixation to the holder fixation tool 26 is realized.

Figure 6:
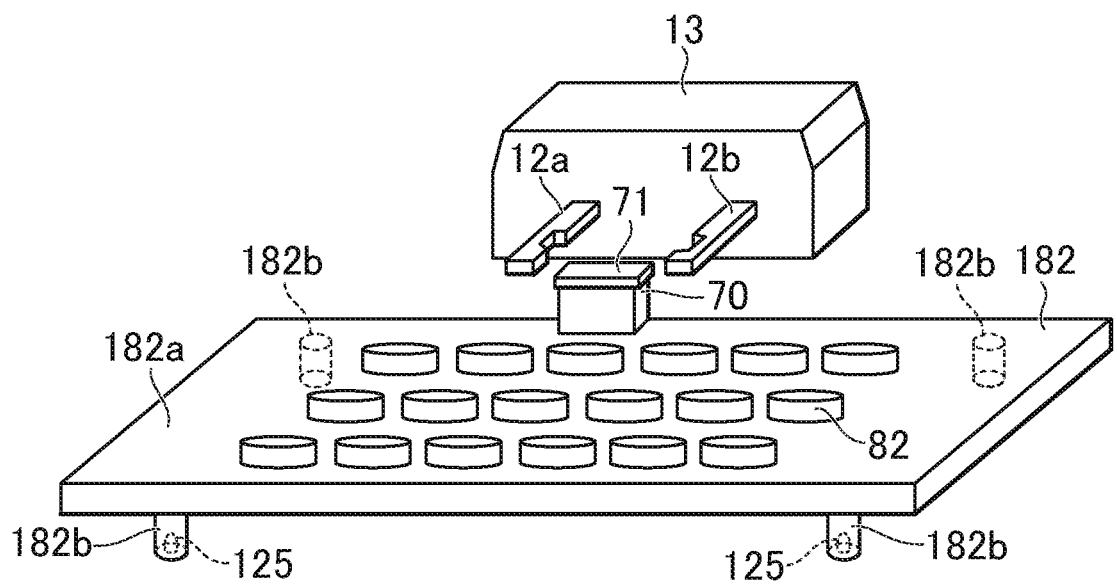
FIG. 6 is a perspective view for illustrating an aluminum cap rack configured to carry aluminum caps.

Moreover, as illustrated in FIG. 6, according to this embodiment, an aluminum cap rack 182 configured to organize and carry the aluminum caps 82 is used. The aluminum cap rack 182 includes a carrying plate 183a configured to carry a plurality of aluminum caps 82, and four support legs 182b extending from a bottom surface of the carrying plate 182a. A hole 125 is formed in a bottom part of the support leg 182a, and the aluminum cap rack 182 is detachably fixed to the holder fixation tool 26 by the pins 25 fitting to the holes 125. Moreover, the gripped portion 70 is mounted to the carrying plate 182a of the aluminum cap rack 182. On the carrying plate 183a, position guidance structures for the carried objects such as recesses or positioning pins may be appropriately provided so as to prevent the aluminum caps 82 from being displaced.

Moreover, according to this embodiment, a rubber plug rack configured to organize and carry the rubber plugs is used. The rubber plug rack is constructed in the same manner as in the aluminum cap rack 182 except that the rubber plugs are carried in place of the aluminum caps 82. Thus, FIG. 6 can be used for reference, and an independent illustration and a redundant description are therefore omitted.

Moreover, according to this embodiment, a vial rack 181 (refer to FIG. 10) configured to organize and carry the vials 81 is used. The vial rack 181 may also be constructed in the same manner as in the aluminum cap rack 182.

Note that, the respective racks having the four support legs such as the vial rack 181, the aluminum cap rack 182, and the rubber plug rack may be configured to be directly arranged on the bottom surface of the work space 21 without providing the holes 125.

A description is now given of the aluminum cap rack 182 and the claws 12a and 12b of the right arm 13 as an example of the use of the claws 12 or 14 to grip the gripped portion 70 provided to the holder configured to hold the work tool and the rack configured to carry the work subjects. FIG. 6 is a perspective view for illustrating the aluminum cap rack configured to carry the aluminum caps, and is a diagram for illustrating the grip of the gripped portion by the claws.

The opening and closing claws 12a and 12b in an open state (separated state) are arranged at a position to clamp the gripped portion 70 of the aluminum cap rack 182. Then, the claws 12a and 12b move toward directions of mutually closing (directions of approaching), thereby gripping the gripped portion 70 of the aluminum cap rack 182. Under this state, the aluminum cap rack 182 can be carried by driving the body 11 and the arm 13 of the robot 10. For example, the aluminum cap rack 182 can be moved from the holder fixation tools 36 in the container booth 30 to the holder fixation tools 26 of the work space 21, and can be moved between the different holder fixation tools 26 in the work space 21.

Note that, the claws 12a and 12b provided to the arm 13 respectively include grooves on sides opposed to each other, and grips the gripped portion 70 by fitting the gripped portion 70 to the grooves, but the configuration is not limited to the configuration according to this embodiment as long as the gripped portion 70 can be gripped. For example, the claw may be configured to have plurality of joints as in the human finger so as to enable the gripping regardless of the shape of the gripped portion.

Further, a description is now given of an operation of the automated manufacturing cell according to this embodiment. The automated manufacturing cell 1 according to this embodiments uses the robot 10 to bring the work tools stored in the respective booths 30, 40, and 50 to the work space 21 in which the work tools are not arranged before the work, and to use the work tools to carry out work on the work subjects. Moreover, according to this embodiment, during the work, the holder configured to hold the work tool is provided so as to be fixed to the holder fixation tools 26 in the work space 21. After the end of the work, the work tools are moved by the robot 10 from the work space 21 to the container booths 30, 40, and 50, and the work space 21 returns to the state in which the work tools are not arranged.

Referring to FIG. 7 to FIG. 11C, a specific description is given of an example of the work carried out in this embodiment. Note that, the work described now is to acquire the vial 81 in which the drug solution is sealed, but is only an example, and the present invention is not limited to this work.

Before the setup switching of the work space 21 and the work on the work subjects using the work tools are automatically carried out by the robot 10, the work tools are prepared manually or by another facility or the like as described below.

First, the open and close door 33 is opened, and the drug solution bottle 91 storing the drug solution, the crimp tool base 193 configured to hold the crimp tool 93, and the vial stand 281 are stored in the container booth 30. On this occasion, the holes 125 provided in the drug solution bottle 91, the crimp tool base 193, and the vial stand 281 are fit to the pins 35, thereby positioning the drug solution bottle 91, the crimp tool base 193, and the vial stand 281, and detachably fixing the drug solution bottle 91, the crimp tool base 193, and the vial stand 281 to the holder fixation tools 36.

Moreover, the open and close door 43 is opened, and the vial rack 181 configured to carry the vials 81 is stored in the container booth 40. On this occasion, the holes 125 provided in the vial rack 181 are fit to the pins 46, thereby positioning the vial rack 181, and detachably fixing the vial rack 181 to the holder fixation tools 46. A plurality of vial racks 181 may be stored by piling the vial racks on top of one another. Pins may be formed on the carrying plate 181a of one vial rack so that the pins are fit to the holes 125 formed in the bottom portions of the support legs of another vial rack. As a result, the piled vial racks 181 are stabilized.

Moreover, the open and close door 53 is opened, and the pipette base 192 configured to hold the body 921 and the tip 923 of the pipette 92, the aluminum cap rack 182 configured to carry the aluminum caps 82, and the rubber plug rack configured to carry the rubber plugs are stored in the container booth 50. On this occasion, the holes 125 formed in the pipette base 192, the aluminum cap rack 182, and the rubber plug rack are fit to the pins 55, thereby positioning the pipette base 192, the aluminum cap rack 182, and the rubber plug rack, and detachably fixing the pipette base 192, the aluminum cap rack 182, and the rubber plug rack to the holder fixation tools 56. A plurality of aluminum cap racks 182 and rubber plug racks may be piled and stored in the same manner as in the vial racks 181.

Then, the sterilization treatment is applied to the work tools and the work subjects stored in the container booths 30, 40, and 50. Note that, the sterilization treatment is applied in all the container booths according to this embodiment, but only at least a part of the container booths needs to include a sterilization area in which the sterilization treatment is to be applied. In other words, depending on the application and types of the work tools and the work subjects to be stored, the container booth and area to which the sterilization treatment is not applied may exist.

Figure 7:
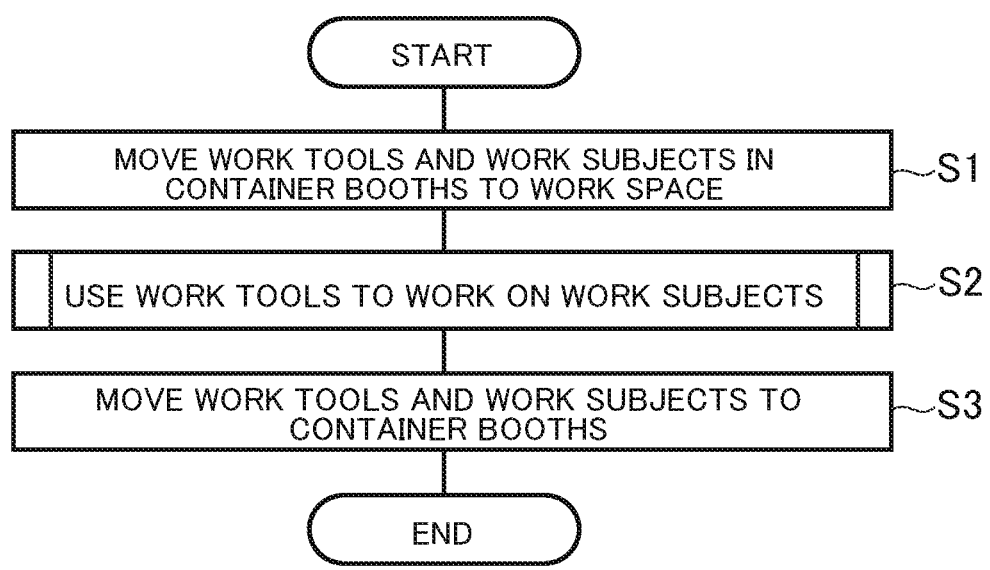
FIG. 7 is a flowchart for illustrating an operation of a robot according to the embodiment.

FIG. 7 is a flowchart for illustrating the operation of the robot according to the embodiment. After the preparation of the work tools before the start of the work, and the end of the sterilization treatment, the robot 10 carries out the setup switching of the work space 21 and the work on the work subjects by using the work tools. The robot 10 is controlled by the controller 60.

Before the work, the holders holding the work tools are fixed only to the holder fixation tools 36 and 56 in the container booths 30 and 50 out of the holder fixation tools 26, 36, 46, and 56 provided in the work booth 20 and the container booths 30, 40, and 50. In other words, before the start of work, any work tools are not provided in the work space 21, and the work space 21 is under a state in which the setup switching can be freely carried out depending on the work content.

In Step S1, the setup controller 61 controls the robot 10 so as to move the work tools and the work subjects in the container booths 30, 40, and 50 to the work space 21. Specifically, the robot 10 controlled by the setup controller 61 carries out the following operation.

First, the robot 10 is controlled to open the open and close door 32 to take out the crimp tool base 193 from the container booth 30, and to move the crimp tool base 193 to the work booth 20. Then, the crimp tool base 193 is detachably fixed to the holder fixation tools 26a by fitting the holes 125a of the crimp tool base 193 to the pins 25a of the work space 21. Note that, according to this embodiment, the open and close door 32 is opened by using one arm to grasp and pulling the outside handle 32a, thereby partially opening the open and close door 32, and then using the other arm to grasp the inside handle 32b, and pushing the open and close door 32 toward an open direction. The open and close doors 42 and 52 described later are similarly opened by using both the arms.

Then, the robot 10 is controlled to take out the drug solution bottle 91 from the container booth 30, and to move the drug solution bottle 91 to the work booth 20. Then, the drug solution bottle 91 is detachably fixed to the holder fixation tools 26d by fitting the holes 125d of the drug solution bottle 91 to the pins 25d of the work space 21. Note that, the gripped portion 70, which is not shown, may also be provided on the drug solution bottle 91, and the drug solution bottle 91 may be transported by using the claws 12 or 14 to grip the gripped portion 70.

Then, the robot 10 is controlled to take out the vial stand 281 from the container booth 30, and to move the vial stand 281 to the work booth 20. Then, the vial stand 281 is detachably fixed to the holder fixation tools 26e by fitting the holes 125e of the vial stand 281 to the pins 25e of the work space 21.

Then, the robot 10 is controlled to close the open and close door 32.

Then, the robot 10 is controlled to open the open and close door 42 to take out the vial rack 181, and to move the vial rack 181 to the work booth 20. Then, the vial rack 181 is detachably fixed to the holder fixation tools 26 by fitting the holes 125 of the vial rack 181 to the pins 25 of the work space 21.

Then, the robot 10 is controlled to close the open and close door 42.

Then, the robot 10 is controlled to open the open and close door 52 to take out the pipette base 192, and to move the pipette base 192 to the work booth 20. Then, the pipette base 192 is detachably fixed to the holder fixation tools 26c by fitting the holes 125c of the pipette base 192 to the pins 25c of the work space 21.

Further, the robot 10 is controlled to take out the aluminum cap rack 182 and the rubber plug rack, and to move the aluminum cap rack 182 and the rubber plug rack to the work booth 20. Then, the aluminum cap rack 182 and the rubber plug rack are respectively detachably fixed to the holder fixation tools 26 by respectively fitting the holes 125 of the aluminum cap rack 182 and the rubber plug rack to the pins 25 of the work space 21.

Then, the robot 10 is controlled to close the open and close door 52.

Figure 8:
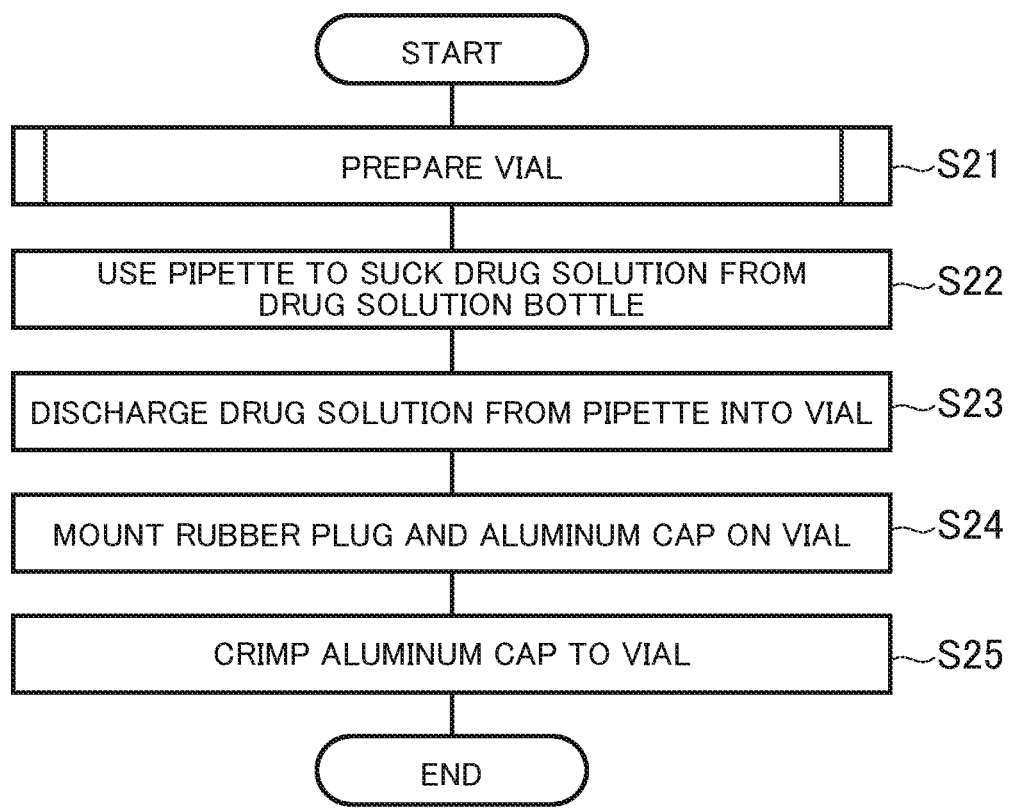
FIG. 8 is a flowchart for illustrating an example of an operation of the robot controlled by a work controller.

In Step S2, the robot 10 is controlled by the work controller 62 to carry out work on the work subjects by using the work tools. Referring to FIG. 8, a description is now given of an example of the operation of the robot controlled by the work controller according to this embodiment.

In Step S2, the vial 81 is prepared. This step includes characteristic control according to this embodiment, and hence a detailed description is given referring to a flowchart of FIG. 9, and FIG. 10 and FIG. 11A to 11C.

Figure 9:
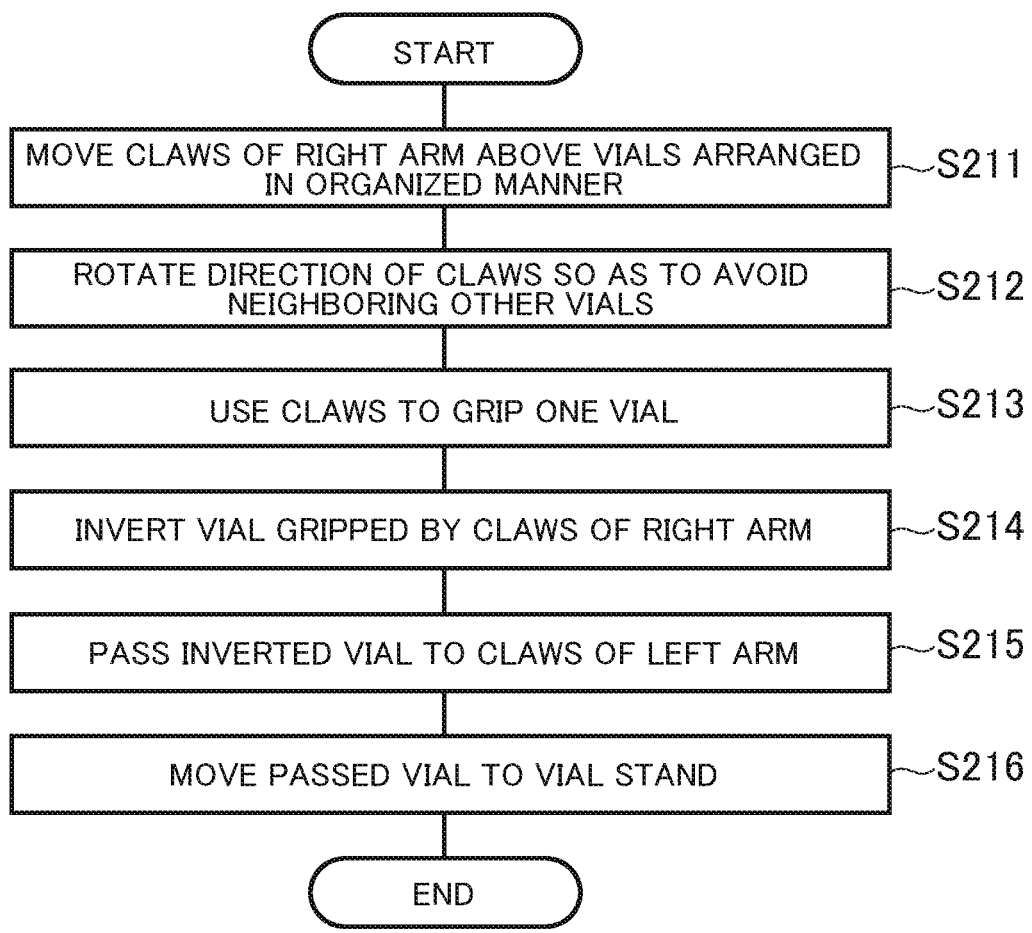
FIG. 9 is a flowchart for illustrating details of a step of preparing a vial.
Figure 10:
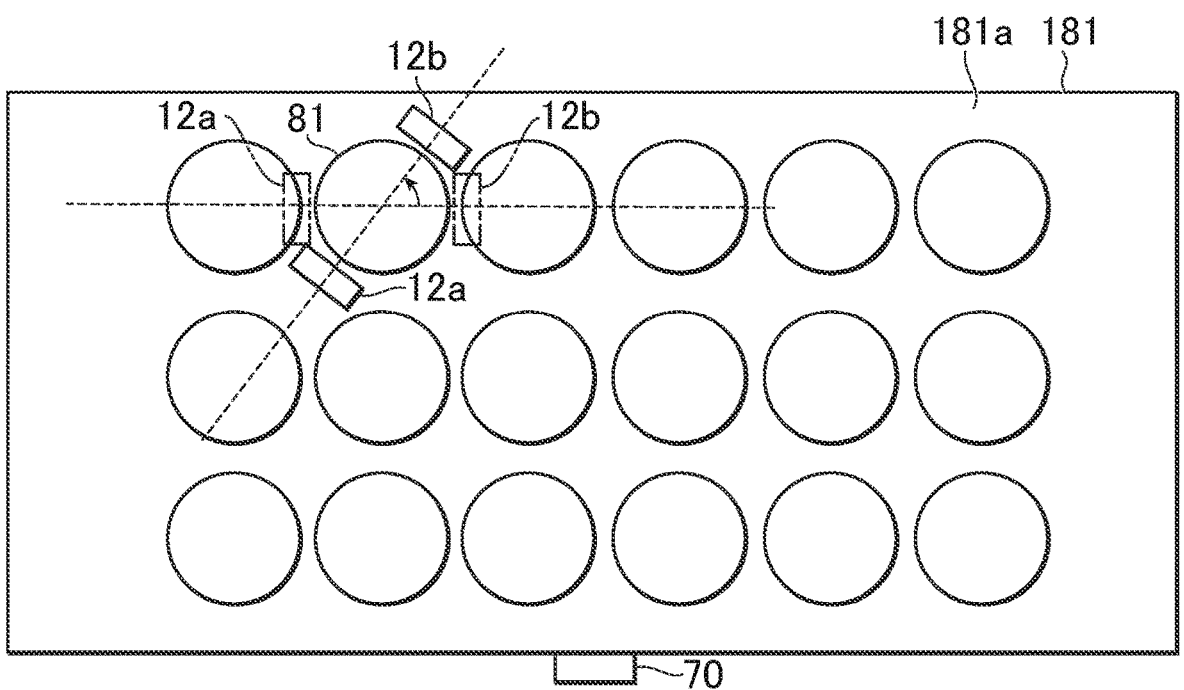
FIG. 10 is a diagram for illustrating a rotation of claws when one of a plurality of vials arranged in an organized manner is gripped.

FIG. 9 is a flowchart for illustrating details of an operation of the robot in the step of preparing the vial. FIG. 10 is a diagram for illustrating a rotation of the claws when one of a plurality of vials arranged in an organized manner is gripped. FIG. 11A to 11C are diagrams for illustrating an operation of inverting the vial gripped by one pair of claws, and passing the vial to the other pair of claws.

In Step S211, the claws 12 of the right arm 13 are moved above in the vertical direction of the plurality of vials 81 arranged in the organized manner on the vial rack 181 (refer to FIG. 11A).

In Step S212, the direction of the claws 12 of the right arm 13 is rotated so as to avoid neighboring other vials. In FIG. 10, the long dashed double-short dashed line represents positions of the claws 12 before the rotation, the arrow represents a rotational direction of the claws 12, and the solid line represents positions of the claws 12 after the rotation. An interference of the claws 12 with other vials is avoided by rotating the claws 12 in this way.

In Step S213, the claws 12 of the right arm 13 are used to grip one of the vials 81 (refer to FIG. 11B).

In Step S214, the vial 81 gripped by the claws 12 of the right arm 13 is inverted by changing the direction of the arm 13 (refer to FIG. 11C). In this way, according to this embodiment, the vial 81 can be inverted without using a dedicated jig or the like.

In Step S215, the inverted vial 81 is passed to the claws 14 of the left arm 15 (refer to FIG. 11C).

In Step S216, the vial 81 passed to the claws 14 of the left arm 15 is moved, and is fit to the hold hole 281b of the vial stand 281 to be held in the hold plate 281a.

Referring again to FIG. 8, a description is further given of the control for the robot 10 by the work controller 62.

While the cap 91a of the drug solution bottle 91 is clamped by the claws 14a and 14b of the left arm 15, the left arm 15 is rotated to loosen the cap 91a. Then, the loosened cap 91a is removed by the claws 14a and 14b of the left arm 15 to open an opening of the drug solution bottle 91.

In Step S22, the robot 10 is controlled to mount the tip 923 on the distal end portion 921a of the body 921 of the pipette 92 to insert the distal end of the tip 923 into the opening of the drug solution bottle 91, to push the push button 922 into the body 921, and to pull the push button 922, to thereby suck the drug solution.

In Step S23, the robot 10 is controlled to push the push button 922 into the body 921 while the distal end of the tip 923 is inserted into the opening of the vial 81 prepared in Step S21, and to discharge the drug solution sucked in Step S22 into the vial 81. Then, the used tip 923 is detached from the body 921, and is held by the hold plate 192a of the pipette base 192. Then, the body 921 from which the tip 923 has been detached is held by the hold plate 192a of the pipette base 192. Then, the robot 10 is controlled to tighten the cap 91a of the drug solution bottle 91.

In Step S24, the robot 10 is controlled to press the rubber plug into the opening of the vial 81 storing the drug solution, and to further mount the aluminum cap 82 on the rubber plug. Note that, when the aluminum cap 82 is gripped by the claws 12 or 14, as described above referring to FIG. 10, the direction of the claws 12 or 14 may be controlled to rotate so as to avoid neighboring other aluminum caps 82. The same holds true for the rubber plug.

In Step S25, the aluminum cap 82 is crimped to the vial 81. Specifically, first, the vial 81 on which the aluminum cap 82 is mounted is gripped by the claws 14 of the left arm 15. Then, the vial 81 is moved to a position at which the aluminum cap 82 mounted on the vial 81 is clamped by the tightening portion 931 of the crimp tool 93. Then, the right arm 13 is used to push the lever 932, thereby operating the tightening portion 931 so that the aluminum cap 82 is tightened to the vial 81.

The robot 10 is controlled to return the vial 81 to which the aluminum cap 82 is crimped to the vial rack 181.

Further, as illustrated in FIG. 7, in Step S3, the robot 10 is controlled by the setup controller 62 so as to move the respective work tools and work subjects from the work space 21 to the container booth 30. On this occasion, the operation period of the robot 10 can be reduced by temporarily placing the plurality of work tools in the temporary placement space 28, and then moving the tools altogether to the container booth 30.

After the operation, the work booth 20 is brought into the state illustrated in FIG. 4 in which no work tools are arranged.

As described above, according to this embodiment, the holder fixation tools 26 configured to detachably holding the holders configured to hold the work tools are provided in the work space 21. Therefore, the quick setup switching by the robot 10 is enabled, and even when work tools to be used are changed depending on the work content, a large-scale construction work does not need to be carried out in the work space 21. As a result, cleaning and sterilization treatment required as a result of the construction work in the work space 21 can be omitted. Moreover, necessity of sterilizing the work space after each setup switching is eliminated by sterilizing, in advance, the various work tools, work subjects, and holders configured to hold the work tools, which are brought into the work space 21, in the container booths 30, 40, and 50 neighboring the work space 21.

Note that, according to the present invention, the work subjects and the work tools to be used are not limited to those described in this embodiment, and various work subjects and work tools may be used depending on the content of the work. For example, according to this embodiment, the vial 81 is described as an example of the work subject, but the work subject is not limited to the vial 81, and may be another container or the like as long as the work subject is a raw material or a part thereof of a product acquired as a result of the work. Moreover, for example, as the work tools, a syringe, a test tube, a tweezers, an electronic balance, and the like may be used for the work. These work tools may include a work tool configured to supply power in the work space 21, and a work tool configured to require a special procedure before the use of the work tool.

Figure 12:
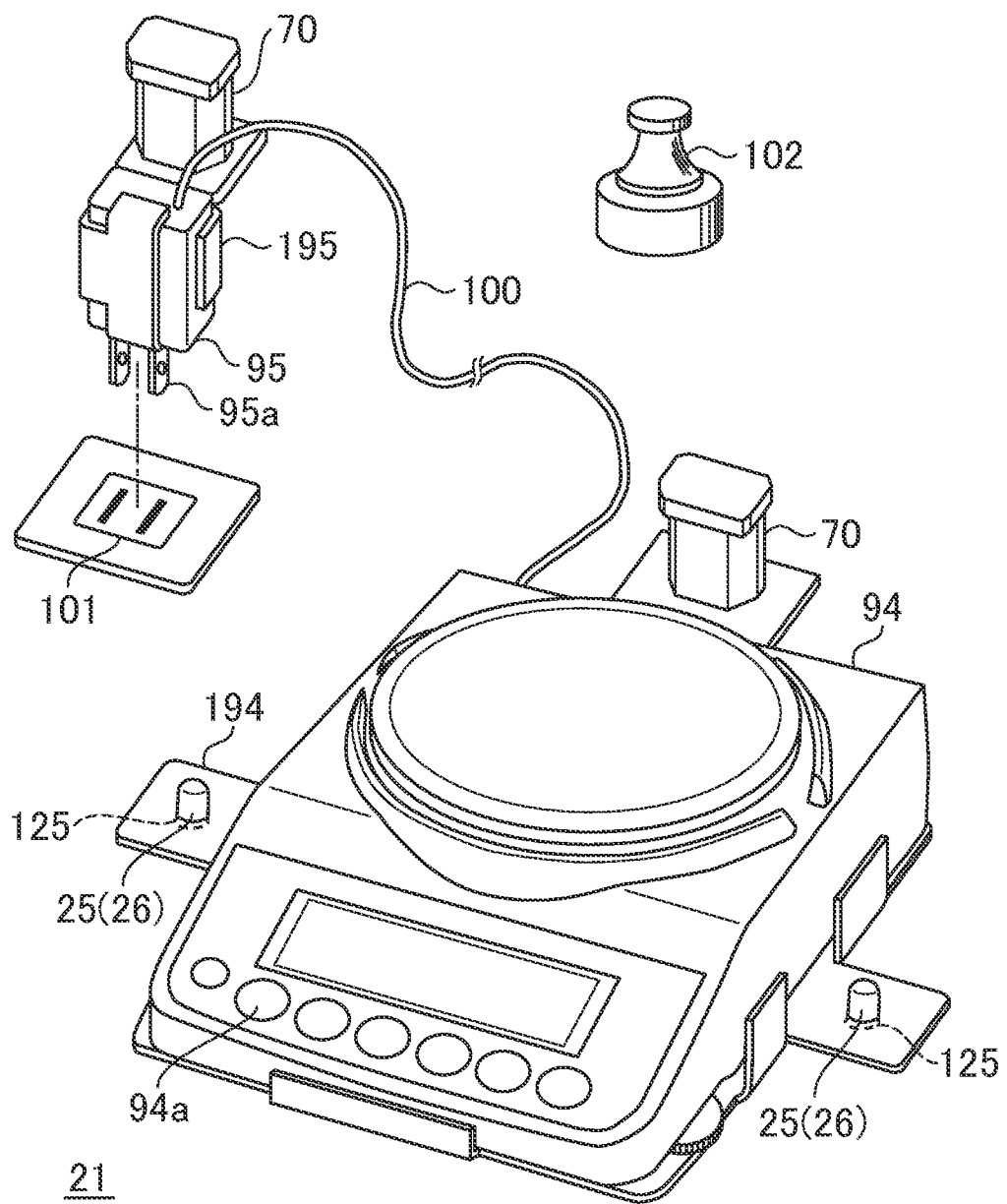
FIG. 12 is a perspective view for illustrating a state of an electronic balance installed in the work space.

As an example of such a tool, a description is now given of an operation of the robot 10 in the automated manufacturing cell 1 when the electronic balance is used in the work space 21. FIG. 12 is a perspective view for illustrating a state of an electronic balance 94 installed in the work space 21. As the electronic balance 94, a special electronic balance for use in the work cell 1 does not always need to be prepared, and can be a general commercially-available electronic balance. In the illustrated example, a holder 194 on which the gripped portion 70 is provided is fixed to the electronic balance 94. The holder 194 has a structure acquired by applying appropriate bending and the like to a sheet metal, and mounting the gripped portion 70 to the sheet metal.

As in the other work tools, the electronic balance 94 is also stored in the container booth 30, 40, or 50, is sterilized depending on necessity, and then, is brought into the work space 21 by the robot 10 upon the work. The robot 10 may use the claws 12 or 14 to grip the gripped portion provided on the holder 194, to thereby handle the electronic balance 94. Moreover, the holes 125 are formed in the holder 194, and the electronic balance 94 is positioned and is detachably fixed by fitting the holes 125 to the corresponding pins 25 on the holder fixation tools 26 provided in the work space 21.

The illustrated electronic balance 94 is supplied with necessary electric power via a cable 100 by connecting an adaptor 95 to a general commercial electric power supply. Thus, to the adaptor 95, an adaptor holder 195 on which the gripped portion 70 is also provided is mounted, and is configured so that the adaptor 95 can be operated by using the claws 12 or 14 of the robot 10 to grip the gripped portion 70 of the adaptor holder 195. The robot 10 brings the electronic balance 94 from the container booth 30, 40, or 50 into the work space 21, then, grips the adaptor 95, and inserts a plug 95a provided on the adaptor 95 into a socket 101 of the commercial electric power supply provided in the work space 21, to thereby supply the electric power to the electronic balance 94. Note that, in FIG. 12, for the sake of easy understanding, the plug 95a and the socket 101 are illustrated as a state in which the plug 95a and the socket 101 are separated from each other.

The electronic balance 94 generally requires calibration before use for a highly precise measurement. Thus, the robot 10 brings the electronic balance 94 into the work space 21, connects the adaptor 95 to the commercial electric power supply, and subsequently, automatically calibrates the electronic balance 94.

When the electronic balance 94 is of a type configured to incorporate weights for the calibration, the electronic balance 94 is calibrated by the robot 10 using the claws 12 or 14 provided at the distal ends of the arms 13 and 15 to operate an operation unit such as a button 94a of the electronic balance 94. In contrast, when the electronic balance 94 is of a type configured to require independent weights for the calibration, an illustrated calibration weight 102 is gripped by the claws 12 or 14, and is placed on the electronic balance 94, and an appropriate operation is then carried out on the button 94a and the like. The calibration weight 102 may be held by the holder 194 along with the electronic balance 94, or may be stored in the container booth 30, 40, or 50 independently of the electronic balance 94.

Moreover, the container of the electronic balance 94 in the container booth 30, 40, or 50 after the work only needs to be carried out in a sequence opposite to that for the preparation thereof. In other words, the robot 10 is controlled to remove the adaptor 95 from the socket 101, then, to grip the gripped portion 70 of the holder 194, and to transport the electronic balance 94 to the container booth 30, 40, or 50.

Note that, when the electronic balance 94 has a function of wireless data communication, a measurement result may be read by the electronic balance 94 by wirelessly receiving a notification of the measured result. Alternatively, another method may be used, such as using an image pickup device such as a digital camera mounted to the arm 13 or 15 of the robot 10 to image the measurement result displayed on a display of the electronic balance 94, to thereby read the measurement result. The imaging device may not only be just mounted to the arm 13 or 15, but may also be stored and prepared in the container booth 30, 40, or 50 as a work device.

Figure 13:
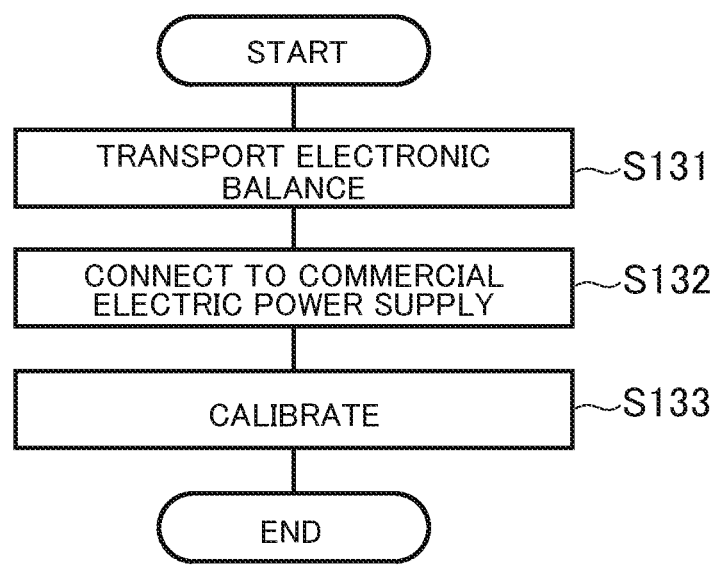
FIG. 13 is a flowchart for illustrating an operation of the robot when the electronic balance is used.

FIG. 13 is a flowchart for illustrating an operation of the robot 10 when the electronic balance 94 is used. The operation of the robot 10 is controlled, and is carried out by the setup controller 61 of the controller 60.

First, in Step S131, the electronic balance 94 stored in the container booth 30, 40, or 50 is transported to a predetermined position of the work space 21. In Step S132, which follows, the electronic balance 94 is connected to the electric commercial power supply. This operation is carried out by the robot 10 connecting the plug 95a provided on the adaptor 95 of the electronic balance 94 or the like to the socket 101 of the commercial electric power supply.

Further, in Step S133, the electronic balance 94 is calibrated. When the electronic balance 94 requires the independent calibration weight 102, this operation may be carried out by an appropriate operation such as the robot 10 placing the calibration weight 102 on the electronic balance 94, and depressing the button 94a. After the end of the calibration, the calibration weight 102 is transported to the initial position. As a result of this operation, the electronic balance 94 is prepared for use in the work space 21.

In the automated manufacturing cell 1, even the work tools requiring the power such as the electric power supply can be prepared for the use in the work space 21 by controlling the robot 10 to carry out the above-mentioned operation. Moreover, a special sequence required before the use of the work tool such as the calibration of the electronic balance 94 in the above-mentioned example can be automatically carried out. Therefore, as the work tool, a general commercially-available product can be used, and hence a special product suitable for the automated manufacturing cell 1 does not need to be prepared. Thus, the cost for the preparation for the work tool can be reduced, and the selection and the update thereof are easy.

Note that, the work by the robot 10 does not need to be carried out by using all the work tools prepared in the work booths, and the work tools dependent on the work subjects and the content of the work only need to be used for the work. Therefore, the automated manufacturing cell 1 can be adapted to various works by stocking various types of work tools in the work booths in advance.

Note that, a scope of the application of the present invention is not limited to the fields of the life-science and medicinal chemistry described in this embodiment, and may be other fields as long as work is carried out by the robot. Even in this case, the setup can be quickly carried out, and a large-scale construction work can be eliminated in the work space by employing such a configuration that the holder fixation tools from which the holder can be detached are provided in the work space. In particular, the automated manufacturing cell according to this embodiment is suitable for an application to multi-type and small-lot production requiring a long period and many man-hours for the setup.

Note that, the holder fixation tool 26 described in this embodiment corresponds to a first holder fixation tool of the present invention, and the holder fixation tools 36, 46, and 56 described in this embodiment correspond to a second holder fixation tool of the present invention. Note that, the holder fixation tools 36, 46, and 56 in the container booths 30, 40, and 50 are not indispensable configurations, but are useful for maintenance of the attitude of the holders and secure positioning. Note that, this embodiment has such a configuration that a pair of the holder fixation tools 26 having the same height, and a pair of the holes 125 formed in the one holder are provided at a predetermined interval. A degree of freedom for the setup of the work space 21 can be enhanced by such design that this interval is unified for the respective holder fixation tools and the respective holders.

It should be understood by those skilled in the art that various modifications, combinations, sub-combinations and alterations may occur depending on design requirements and other factors insofar as they are within the scope of the appended claims or the equivalents thereof.

What is claimed is:

1. A life-science and/or medicinal chemistry automated manufacturing cell, comprising:
   a work booth provided with a work space, the work booth configured to be kept in an aseptic state;
   a robot arranged in the work booth, the robot controlled by a controller;
   a container booth configured to store a work tool and a work subject for life-science and/or medicinal chemistry, the container booth connected to the work booth via a first door and connected to an external space via a second door, the first and second doors configured to close and seal the container booth from the work booth and from the external space, respectively; and
   a first holder fixation tool arranged and fixed in the work space relative to where the robot is fixed to the work space, the first holder fixation tool configured to detachably fix a holder configured to hold the work tool,
   wherein the container booth comprises a sterilizer, and
   wherein the first holder fixation tool protrudes from a bottom surface of the work space, the first holder fixation tool comprises a plurality of the first holder fixation tools, and
a first height from the bottom surface of the work space of one first holder fixation tool among the plurality of the first holder fixations tools is different from a second height from the bottom surface of the work space of another first holder fixation tool among the plurality of the first fixation tools.

2. The life-science and/or medicinal chemistry automated manufacturing cell according to claim 1, wherein the controller comprises:
a setup controller configured to control the robot so that the robot moves the holder from the container booth to the work space; and
a work controller configured to control the robot so that, in the work space, the robot uses the work tool to work on the work subject.

3. The life-science and/or medicinal chemistry automated manufacturing cell according to claim 2, wherein:
the work tool dependent on one of the work subject and a content of the work is arranged in the container booth before a start of the work; and
the setup controller is configured to control the robot to move the work tool dependent on one of the work subject and the content of the work from the container booth to the work space.

4. The life-science and/or medicinal chemistry automated manufacturing cell according to claim 3, wherein the setup controller is configured to control the robot to connect to the work tool so that power is supplied to the work tool in the work space.

5. The life-science and/or medicinal chemistry automated manufacturing cell according to claim 4, wherein:
the work tool is an electronic balance; and
the setup controller is configured to control the robot to calibrate the electronic balance in the work space.

6. The life-science and/or medicinal chemistry automated manufacturing cell according to claim 1, further comprising a second holder fixation tool arranged and fixed in the work space relative to where the robot is fixed to the work space, the second holder fixation tool configured to detachably fix the holder.

7. The life-science and/or medicinal chemistry automated manufacturing cell according to claim 6, wherein, before a start of the work, the holder is provided by being fixed only to the second holder fixation tool out of the first holder fixation tool and the second holder fixation tool.

8. The life-science and/or medicinal chemistry automated manufacturing cell according to claim 1, wherein:
the robot comprises at least a pair of claws configured to open and close; and
the life-science and/or medicinal chemistry automated manufacturing cell further comprises a gripped portion which is mounted to each of a plurality of the holders, and to be gripped by the pair of claws.

9. The life-science and/or medicinal chemistry automated manufacturing cell according to claim 2, wherein:
the robot comprises at least a pair of claws configured to open and close; and
the work controller is configured to control, when one of a plurality of work subjects is gripped, the robot to rotate a direction of the pair of claws so as to avoid another neighboring work subject.

10. The life-science and/or medicinal chemistry automated manufacturing cell according to claim 2, wherein:
the robot comprises at least two arms each comprising at least a pair of claws configured to open and close; and
the work controller is configured to control the robot so that the robot uses the pair of claws of one of the at least two arms to grip and invert the work subject, and then pass the work subject gripped by the one of the at least two arms to another of the at least two arms.

11. The life-science and/or medicinal chemistry automated manufacturing cell according to claim 1, further comprising:
a temporary placement space provided inside the work booth and outside the work space and a movable range of the door;
wherein the first door is configured to be opened and closed by the robot.

12. The life-science and/or medicinal chemistry automated manufacturing cell according to claim 1, wherein:
the first holder fixation tool comprises a pin; and
the holder has a hole to which the pin is to fit.

13. A life-science and/or medicinal chemistry automated manufacturing method, comprising:
storing, before a start of work, a work tool and a work subject for life-science and/or medicinal chemistry in a container booth, the container booth connected to a work booth via a first door and an external space via a second door, the first and second doors configured to close and seal the container booth from the work booth and from the external space, respectively, the work booth comprising a work space and a robot;
controlling, by a setup controller, the robot to move the work tool and the work subject from the container booth to the work space;
controlling, by the setup controller, the robot to fix a holder to a first holder fixation tool, the first holder fixation tool is arranged and fixed in the work space relative to where the robot is fixed to the work space, and is configured to detachably fix the holder configured to hold the work tool;
controlling, by a work controller, the robot to use the work tool to work on the work subject,
sterilizing the work tool with a sterilizer which is comprised in the container booth; and
wherein the first holder fixation tool protrudes from a bottom surface of the work space,
the first holder fixation tool comprises a plurality of the first holder fixation tools, and
a first height from the bottom surface of the work space of one first holder fixation tool among the plurality of the first holder fixations tools is different from a second height from the bottom surface of the work space of another first holder fixation tool among the plurality of the first fixation tools.

14. The life-science and/or medicinal chemistry automated manufacturing method according to claim 13, further comprising:
controlling the robot to move the holder fixed to the first holder fixation tool from the work space to the container booth, and fix the holder to a second holder fixation tool.

15. A manufacturing cell, comprising:
a work booth provided with a work space, the work booth configured to be kept in an aseptic state;
a robot arranged in the work booth;
a container booth configured to store a work tool and a work subject, the container booth connected to the work booth via a first door and connected to an external space via a second door, the first and second doors configured to close and seal the container booth from the work booth and from the external space, respectively; and a first holder fixation tool arranged and fixed in the work space relative to where the robot is fixed to the work space, the first holder fixation tool is configured to detachably fix a holder configured to hold the work tool, wherein the container booth comprises a sterilizer, and wherein the first holder fixation tool protrudes from a bottom surface of the work space, the first holder fixation tool comprises a plurality of the first holder fixation tools, and a first height from the bottom surface of the work space of one first holder fixation tool among the plurality of the first holder fixations tools is different from a second height from the bottom surface of the work space of another first holder fixation tool among the plurality of the first fixation tools.

16. The life-science and/or medicinal chemistry automated manufacturing cell according to claim 1, wherein the sterilizer being one selected from the group consisting of a dry heat sterilizer, an autoclave, a chemical clave, and an ultraviolet sterilizer and a radiation sterilizer.

17. The life-science and/or medicinal chemistry automated manufacturing cell according to claim 16, wherein said sterilizer is a dry heat sterilizer.

18. The life-science and/or medicinal chemistry automated manufacturing cell according to claim 16, wherein said sterilizer is an autoclave.

19. The life-science and/or medicinal chemistry automated manufacturing cell according to claim 16, wherein said sterilizer is a chemical clave.

* * * * *